United States Patent [19]

Pugia et al.

[11] Patent Number: 5,173,431
[45] Date of Patent: Dec. 22, 1992

[54] COPPER OXIDATION PROTEIN ASSAY

[75] Inventors: Michael J. Pugia, Granger, Ind.; Michael Salvati, St. Paul, Minn.

[73] Assignee: Miles Inc., Elkhart, Ind.

[21] Appl. No.: 790,429

[22] Filed: Oct. 12, 1991

[51] Int. Cl.$^5$ ............................................. G01N 33/48
[52] U.S. Cl. ...................................... 436/86; 436/164; 436/805; 422/56; 558/162; 558/209
[58] Field of Search ................ 436/86, 15, 63, 87–88, 436/164, 805; 422/56–58; 558/156, 162, 209

[56] References Cited

PUBLICATIONS

Yamamoto et al., Int. J. Biol. Macromol., 1980 vol. 2, Aug. pp. 263–265 "Catalytic actions of synthetic polypeptides: 1. Decomposition of hydrogen peroxide by the poly(L-glutamic acid)-copper (II) complex".
Mack et al., J. Am. Chem. Soc. 1988 vol. 110, pp. 7572–7574 Design and Chemical Synthesis of a Sequence-Specific DNA–Cleaving Protein.

Primary Examiner—James C. Housel
Assistant Examiner—Lyle A. Alexander
Attorney, Agent, or Firm—Jerome L. Jeffers

[57] ABSTRACT

A procedure for detecting proteins in fluids (particularly body fluids) which involves contacting such fluid with a composition comprising copper in a form capable of forming a copper/protein complex, a peroxide and a redox indicator which provides a detectable response when oxidized, together with an ionizable phosphate containing compound to prevent interference with the redox indicator from substances present in the fluid.

12 Claims, 2 Drawing Sheets

COPPER OXIDATION PROTEIN ASSAY

BACKGROUND OF THE INVENTION

The present invention is a novel methodology for colormetrically determining the concentration of protein in aqueous media such as certain biological fluids.

The detection of protein in biological fluids such as blood serum and urine is useful in the diagnosis of various abnormalities. For example, in the case of blood serum, both the total protein and the ratio of individual protein fractions may change independently of one another in disease states. Thus, in the case of dehydration, total protein may increase 10 to 15 percent from its normal concentration of approximately 6.8 to 8.8 gm/100 mL, with the increased level being reflected in all protein fractions. Dehydration may result from a decrease in water intake or from excessive water loss as occurs in severe vomiting, diarrhea, Addison's disease and diabetic acidosis. Hypoproteinemia, characterized by total protein levels below 6.0 gm/100 mL is encountered in many unrelated disease states. For example, in the nephrotic syndrome, large masses of albumin may be lost in the urine as a result of leakage of the albumin molecules through the damaged kidney. In salt retention syndromes, water is held back to dilute out the retained salt, resulting in the dilution of all protein fractions. Large quantities of proteins are lost in patients with severe burns, extensive bleeding or open wounds. A long period of low intake or deficient absorption of protein may affect the level and composition of serum proteins, as in sprue and in other forms of intestinal malabsorption as well as in acute protein starvation.

All urines contain some protein. The protein excreted by healthy individuals is on the order of 50 to 100, sometimes as high as 150 mg/24 hour. After considerable muscular exertion, this value may be as high as 250 mg. Proteinuria is said to be present whenever the urinary protein output is greater than that reflected in these normal values. Not all proteinuria is clinically significant, but persistent abnormal levels of protein in the urine is an indicator of the presence of kidney and urinary tract disease. For example, proteinuria may be associated with the early stages of such diseases as pyelonephritis, reflecting bacterial infection in the kidney, and acute glomerulonephritis, often associated with recent streptococcal infections. Proteinuria is associated with certain other disease states which tend to cause kidney lesions such as lupus erythematosus, amyloidosis, toxemia of pregnancy, septicemia and certain forms of drug and chemical poisoning. Thus, the detection of urinary protein and the quantitative assessment of the degree of proteinuria are very important laboratory procedures.

The peroxidase activity of copper protein complexes has been cited in the literature, H. Yamamoto et al *Int. J. Biol. Macromol.*, 2 (4), 263-265, (1980); D. P. Mack et al, *J. Am. Chem. Soc.*, 110, 7572-7574 (1989). Thus, protein bound copper can be used to produce a colored response by catalyzing the oxidation of a redox indicator such as 3,3',5,5'-tetramethylbenzidine by a hydroperoxide. However, it has been discovered that the application of the peroxidase-like activity of the copper protein complex to detect protein in biological fluids, especially serum and urine containing high concentrations of protein, is limited by interferents present in these fluids.

It would be desirable and it is an object of the present invention to provide a method for the determination of proteins in aqueous fluids which involves the peroxidase like activity of protein-copper complexes.

It is a further object to provide such a method in which the interference of components in certain bodily fluids with protein determination is reduced or eliminated.

SUMMARY OF THE INVENTION

The present invention is a method for the detection of a protein in a fluid system. The method involves contacting a fluid suspected of containing proteinaceous material with copper, in a form capable of forming a copper/protein complex, a peroxide and a redox indicator which produces a detectable response when oxidized by the peroxide in the presence of the copper/protein complex. Since biological fluids, particularly blood serum, contain components which interfere with the redox indicator, there is added to the system a composition containing ionizable phosphate to prevent such interference which is:

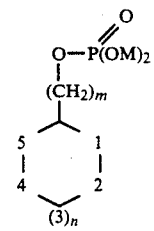

wherein 2, 3, 4 and 5 are

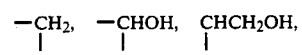

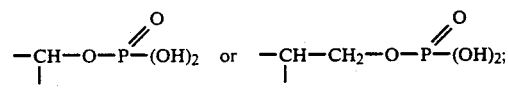

1 is any of the above or —O— and m and n are independently 0 or 1; or

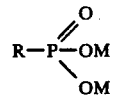
B.

wherein R is OH or substituted or unsubstituted phenyl and, in each case, M is hydrogen or a metallic cation.

Also included within the scope of the present invention is a reagent system which comprises copper in a form capable of forming a copper/protein complex when contacted with the protein in solution, a peroxide, a redox indicator which produces a detectable response when oxidized by the peroxide in the presence of the peroxidatively active copper/protein complex and a compound for preventing interference with the system as described above.

DESCRIPTION OF THE INVENTION

Figure 1:
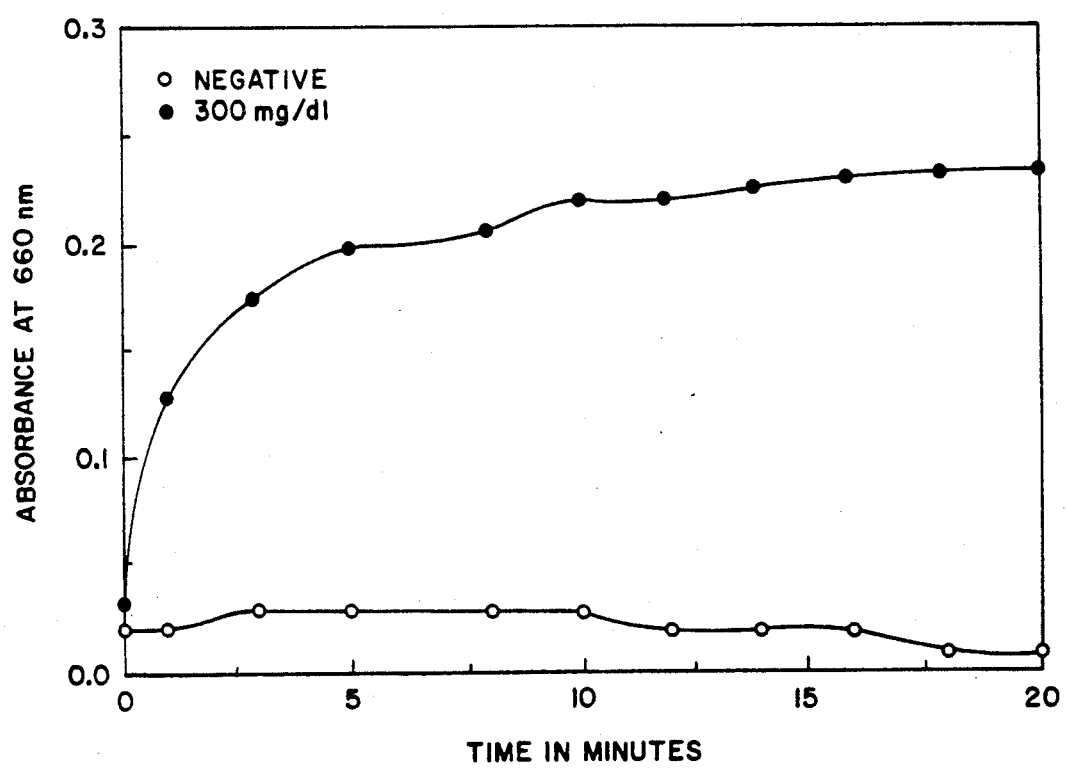
FIG. 1 is a graphical representation of absorbance as a function of time.

The peroxidase activity of copper protein complexes has been cited in the literature. Thus, one could envision a detection system for proteins in an aqueous fluid using $CuSO_4$ as the copper source and tetramethylbenzidine (TMB) as redox indicator represented by the reaction sequence:

$$CuSO_4 + Protein \rightarrow Cu\ Protein + SO_4^-$$

$$H^+ + ROOH + TMB \xrightarrow{Cu\ Protein} ROH + [TMB.^+] + HO^-$$

where the peroxidatively active Cu Protein complex catalyzes the oxidation of TMB by a peroxide [ROOH] to produce the oxidized form of the redox indicator [TMB.+] to thereby provide a colormetrically detectable response to the presence of the protein. However, such a system is of little value in biological fluids because of the high concentration of positive interferents in such fluids.

The present invention deals with this problem by adding to the reagent system certain ionizable phosphate containing compounds which retard the action of interferents present in the biological fluid. Typical substances present in urine or blood serum which tend to interfere with the Cu Protein complex redox reaction described above include creatinine, uric acid, ammonium, histidine, arginine, lysine and ornithine. It has been discovered that their interference can be essentially eliminated by the addition of certain ionizable phosphate containing compounds to the reagent system to thereby render the ability of copper and proteins to form a peroxidatively active complex useful for the detection of the protein.

Suitable ionizable phosphate containing compounds include phosphate attached to an alkyl ring as represented by the formula:

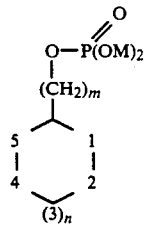
A.

In the above formula, 2,3,4 and 5 are $$-CH_2, \quad -CHOH, \quad -CHCH_2OH,$$

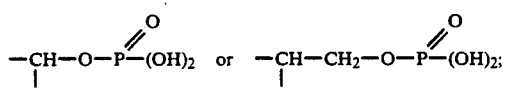

1 is any of the above or —O— and m and n are independently 0 or 1. Typical of preferred inhibitors are phytic acid where m is 0; n is 1 and positions 1 through 5 are

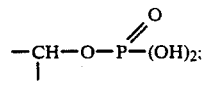

6-glucose phosphate where m is 1, n is 1, positions 2-5 are

and position 1 is —O— and 1-glucose phosphate where m is 0 and n is 1, positions 2-5 are

and position 1 is —O—. The examples in case A are limited to phosphates attached to either a cyclohexane ring or a carbohydrate. This is the case because it has been discovered that aromatic phosphates such as phenyl and naphthalene phosphate are not effective. In addition, linear alkyl phosphates such as glycerol and amino ethyl phosphate have not proven effective in the present system. However, five membered ring compounds characterized by the above formula where n is 0 such as D-ribose-5-phosphate, 6-ribose-1-phosphate, 2,4-cyclopentane diphosphate, and 1,4-anhydro-L-threitol diphosphate can be used as interference inhibitors in the system of this invention.

Another class of inhibitors which have been found to be suitable for use in the present invention are phosphate and phenyl phosphoric acid of the formula:

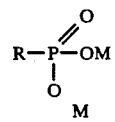
B.

where R is OH or phenyl which may be substituted with substituents such as; for example, halogen, hydroxyl, nitro, cyano and acetyl. Alkyl phosphoric acids such as ethyl, amino ethyl and carboxyethyl phosphoric acids as well as derivatives of phosphate such as pyrophosphate and phosphorous acid are not effective in this reagent system.

In both cases A and B the free acid, i.e. P—OH or the salt form, e.g. P—O⁻M⁺ where M⁺ is, for example lithium, sodium, ribidium, cesium, magnesium, calcium, strontium or barium may be used without impairing the effectiveness of the phosphate.

Aside from the phosphate interference inhibitor, the present reagent system requires a source of cuprous ion, a peroxide and a redox indicator. Suitable copper sources include the sulfate, acetate, citrate, oxalate, phosphate and tartrate salts; chelated copper such as copper complexed with one or more chelating agents is not suitable.

Suitable peroxides include cumene hydroperoxide, t-butyl hydroperoxide, diisopropylbenzene hydroperoxide, 1-hydroxycyclohexane-1-hydroperoxide, 2,5-dimethylhexane-2,5-dihydroperoxide, paramenthane hydroperoxide, 1,4-diisopropylbenzene monohydroperoxide, p-t-butylisopropylbenzene hydroperoxide, 2-(α-hydroperoxyisopropyl)-6-isopropylnaphthalene, tetralin hydroperoxide or combinations thereof.

Redox indicators include, for example, benzidine; o-tolidine; a 3,3',5,5'-tetraalkylbenzidine, wherein the alkyl group contains from one to about six carbon atoms; o-dianisidine; 2,7-diaminofluorene; bis-(N-ethylquinol-2-one)-azine; (N-methylbenzthiazol-2-one)-(1-ethyl-3-phenyl-5-methyltriazol-2-one)-azine; or combinations thereof.

Typically, the reagent system is dissolved in water. However, as illustrated by the examples, organic solvents can be incorporated into the system provided the ionization of the phosphate is not affected thereby.

For so-called wet chemistry analysis, the test composition is used as a liquid or as a solid which is dissolvable in water or another suitable solvent to provide a reagent solution. Where the reagent consists of individual components, such can be mixed together to form a final reaction solution. After mixing the sample (for example, substrate solution, enzyme solution, blood, serum, plasma or urine) with an aliquot of the reagent, the resulting color is measured using a photometer and the respective analyte concentration is calculated by means of the molar extinction coefficients and the reagent or sample volumes added.

The reagent composition can also be incorporated into a carrier matrix in the form of a reagent strip. Suitable carrier matrices are known in the art and include absorbent papers, woven and nonwoven cloth, glass fiber filters, polymeric membranes and films. Incorporation methods include impregnation of a formed carrier matrix with a solution, suspension, or other liquid form of the test composition, in one or more steps, followed by drying of the matrix; and formation of a matrix in the presence of one or more of the components of the test composition, e.g., by casting or layering solutions of film or membrane forming formulations. Absorbent or swellable carriers such as filter paper or absorbent glass fiber filters or synthetic nonwovens are impregnated or sprayed with these solutions and then dried. The test composition can also be incorporated into carrier matrices which have been prepared from casting solutions. Cellulose, cellulose derivatives, gelatin, gelatin derivatives or, alternatively, porous plastics such as polyurethane and acrylamide may be included by way of example.

Typically, the concentrations of the various reagents in the system will range from about 5 to 100 millimoles peroxide, 1 to 20 millimoles Cu++ and 1 to 100 millimoles of the ionizable phosphate per liter of reagent composition. This solution can either be used as is in a wet reagent test or applied to the reagent strips previously described in the production of the dry test strips.

The method of practicing the present invention is further illustrated by the following examples:

EXAMPLE 1

General Procedure—An aqueous copper solution is combined with an aqueous test sample with or without albumin, a TMB acetonitrile solution and a DBDH acetonitrile solution. The combined solution is mixed and the absorbance of the resultant blue color produced at 660 nm after one minute is determined using a Gilford Response II UV-VIS Spectrophotometer and recorded. The albumin used is Pentex human albumin obtained from Fraction IV in which no peroxidatively active hemoglobin contamination was detectable. The concentrations of each element of the various formulations is as follows:

| Component | Stock Concentration nM | Volume mL |
| --- | --- | --- |
| Copper salts (Table 2) | 8.4 | 1.0 |
| Boric Acid Buffer at pH 8.2 ± 200 mg/dL Albumin | 240.0 | 0.5 |
| Tetramethylbenzidine [TMB] | 156.3 | 1.0 |
| Diisopropylbenzene dihydroperoxide [DBDH] | 37.6 | 0.2 |

Results: The addition of albumin to copper sulfate and DBDH stimulates the oxidation of TMB which produced blue absorbance and represents a protein effect (Table 1).

TABLE 1

| The Protein Effect | |
| --- | --- |
| ALBUMIN mg/dL | ABS |
| 0 | 0.020 |
| 2 | 0.151 |
| 6 | 0.228 |
| 8 | 0.348 |
| 16 | 0.456 |

The absorbance (ABS) produced is directly proportional to protein concentration with a protein concentration of 2 mg/dl being easily detected. The catalytic effect of protein requires the presence of copper at a pH greater than 5.0 and is increased with increasing pH. The slight absorbance observed with the blank was due to the copper sulfate's blue color and can be substracted out for accuracy. The counter anion of the metal salt has a profound influence on the protein effect (Table 2).

TABLE 2

| The Influence of Copper Salt on Protein Effect | | | |
| --- | --- | --- | --- |
| | NO ALBUMIN ABS | 66 mg/dL ALBUMIN ABS | Δ ABS |
| Cu(II) Sulfate | 0.069 | 0.926 | 0.86 |
| Cu(II) Acetate | 0.242 | 1.084 | 0.84 |
| Cu(II) Citrate | 0.163 | 0.916 | 0.75 |
| Cu(II) Oxalate | 0.368 | 1.128 | 0.76 |
| Cu(II) Phosphate | 0.479 | 1.010 | 0.53 |
| Cu(II) Tartrate | 0.040 | 0.300 | 0.26 |
| Cu(II) EDTA | 0.010 | 0.010 | 0.00 |
| Cu(II) EGTA | 0.010 | 0.010 | 0.00 |
| Cu(II) HEDTA | 0.010 | 0.010 | 0.00 |
| Cu(II) DTPA | 0.063 | 0.082 | 0.02 |

Polycarboxyamine counter-anions are abbreviated as EDTA, EGTA, HEDTA and DPTA.

Polycarboxyamine counter anions such as EDTA completely inhibit the protein effect by strongly chelating copper. The sulfate counter anion is preferred because it has a low blank color and gave the largest absorbance increase upon the addition of aqueous albumin.

Accordingly, the application of copper sulfate in the detection of urinary albumin was then investigated. This system was found to be reactive to normal urinary components as is demonstrated by Table 3 with aqueous solutions of compounds present in normal urine. Ammonium, uric acid and creatinine all produced false positive reactions but phosphate decreased the background reaction (Table 3).

TABLE 3

Reactivity Toward Urine Components

| URINE COMPONENT | NO ALBUMIN ABS | 33 mg/dL ALBUMIN ABS* |
|---|---|---|
| None | 0.07 | 0.481 |
| Oxalate | 0.08 | 0.426 |
| CaCl$_2$ | 0.06 | 0.481 |
| NaCl | 0.07 | 0.418 |
| Creatinine | 4.00 | 3.966 |
| Citric Acid | 0.07 | 0.462 |
| Urea | 0.09 | 0.495 |
| Phosphate | 0.01 | 0.274 |
| Ammonium | 1.09 | 1.661 |
| Uric Acid | 0.52 | 1.195 |

*Absorbance recorded in presence of albumin and urine component.

The observation that phosphate reduced background reactivity led to the second part of this invention discussed in the next example. It was also found that basic amino acids were very reactive in the copper sulfate systems (Table 4).

TABLE 4

Reactivity Toward Amino Acids, Peptides and Proteins

| PEPTIDE (16.8 mM) | ABS |
|---|---|
| None | 0.07 |
| Poly-Ornithine | 1.17 |
| Poly-D-Lysine | 0.64 |
| Poly-L-Lysine | 0.81 |
| Poly-L-Arginine | 0.36 |
| Poly-L-Histidine | 2.68 |
| Poly-Glycine | 0.09 |
| GLYGLYGLY | 0.08 |
| GLYGLYHIS | 0.08 |
| L-Histidine | 1.15 |
| Albumin | 0.98 |
| IgG | 0.31 |

The data of Table 4 illustrates the positive interference of amino acids with the system.

EXAMPLE 2

Demonstration of Phosphates as Inhibitors of Positive Interferences

The use of phosphate inhibitors is demonstrated with two procedures. Procedure one uses acetonitrile and water as the solvent system with a one to three dilution of the sample. Procedure two uses dimethylformamide and water as the solvent system with a one to five dilution of the sample.

Procedure 1: An aqueous copper solution is combined with a natural or synthetic urine sample, an aqueous phosphate inhibitor solution (see Table 5), a TMB acetonitrile solution and a DBDH acetonitrile solution.

TABLE 5

The Influence of Phosphate Inhibitors on Background Reactivity[1] and on the Protein Effect with 66 mg/dL Albumin

| Phosphate Compound | % Inhibition of Blank Reactivity | PROTEIN EFFECT[2] ABS |
|---|---|---|
| No phosphate compound | 0 | −0.08 |
| Diphenyl Phosphate | 6 | −0.06 |
| Phenyl Phosphate | 5 | −0.03 |
| Nitrophenyl Phosphate | 3 | −0.04 |
| Naphthyl Phosphate | 2 | −0.05 |
| Phytic Acid | 100 | 0.11 |
| 6-Glucose Phosphate | 67 | 0.05 |

TABLE 5-continued

The Influence of Phosphate Inhibitors on Background Reactivity[1] and on the Protein Effect with 66 mg/dL Albumin

| Phosphate Compound | % Inhibition of Blank Reactivity | PROTEIN EFFECT[2] ABS |
|---|---|---|
| 1-Glucose Phosphate | 81 | 0.11 |
| Phosphate | 67 | 0.06 |
| Aminoethyl Phosphate | 31 | −0.06 |
| Glycerol Phosphate | 56 | 0.00 |
| Phosphorous Acid | 10 | −0.02 |
| Pyrophosphate | 90 | −0.02 |
| Phenyl Phosphonic Acid | 53 | 0.07 |
| Ethylphosphonic Acid | 49 | −0.02 |
| Aminoethyl Phosphonic Acid | 71 | 0.00 |
| Carboxylethyl Phosphonic Acid | 42 | 0.00 |

[1] Blank reactivity of synthetic urine containing ammonium, creatinine, and uric acid at their highest physiological concentrations.
[2] The change in absorbance upon the addition of 66 mg/dL albumin.

The combined solution is mixed and the absorbance of the resultant blue color produced at 660 nm after five minutes is recorded.

| Component | Stock Concentration mM | Volume mL |
|---|---|---|
| Copper Sulfate | 8.4 | 1.0 |
| Phosphate inhibitor @ pH 8.2 | 25.0 | 0.5 |
| Sample @ pH 8.2 | — | 1.0 |
| Tetramethylbenzidine (TMB) | 156.3 | 1.0 |
| Diisopropylbenzene dihydroperoxide (DBDH) | 37.6 | 0.2 |

Procedure 2: An aqueous copper phytic acid solution is combined with a urine sample adjusted to pH 8.2 and a dimethylformamide solution of TMB and DBDH. The combined solution is mixed and the absorbance of the resultant blue color produced at 660 nm is recorded at 5 minutes.

| Component | Stock Concentration nM | Volume mL |
|---|---|---|
| Copper sulfate and phytic acid | 0.7 + 4.1 | 2.0 |
| Sample at pH 8.2 TMB and DBDH | 7.1 + 6.3 | 1.0 |

Results: The blank reactivity observed with normal urine components such as creatinine, ammonium and uric acid prevented the measurement of urinary albumin of Procedure 1. The measurement of urinary albumin was accomplished when it was discovered that several organic phosphates reduced the blank reactivity due to creatinine, ammonium and uric acid while maintaining reactivity towards protein (Table 5). Of these organic phosphates, phytic acid was selected and used in Procedure 2. Phytic acid caused the greatest inhibition of blank reactivity while allowing the highest reactivity of albumin. Further reactivity of amino acids and peptides was also inhibited (Table 6).

TABLE 6

Reactivity of Copper-Phytic Acid System Towards Amino Acids, Peptides and Proteins

| PEPTIDE (16.8 mM) | ABS[1] |
|---|---|
| None | 0.01 |
| Poly-Ornithine | 0.01 |

TABLE 6-continued

| Reactivity of Copper-Phytic Acid System Towards Amino Acids, Peptides and Proteins | |
|---|---|
| PEPTIDE (16.8 mM) | ABS[1] |
| Poly-D-Lysine | 0.01 |
| Poly-L-Lysine | 0.01 |
| Poly-L-Arginine | 0.01 |
| Poly-L-Histidine | 0.01 |
| Poly-Glycine | 0.01 |
| GLYGLYGLY | 0.00 |
| GLYGLYHIS | 0.01 |
| L-Histidine | 0.03 |
| Albumin | 0.27 |
| IgG | 0.16 |

[1]Sample solution contains 16.8 mM amino acid, peptide or protein and lacks any urinary components.

Specificity of this assay was further demonstrated in natural urine (Table 7). The addition of 0.405 mg/dL hemoglobin to the urine samples did not produce false positive results while the addition of 50 mg/dL ascorbate to urine samples containing a protein did not produce false negative results. The system is also relatively insensitive to SG in the range studied (Table 7).

TABLE 7

| | Reactivity in Natural Urine Samples | | |
|---|---|---|---|
| | ABSORBANCE | | |
| SAMPLE | SG 1.005 mean (sd) | SG 1.009 mean (sd) | SG 1.019 mean (sd) |
| Urine | 0.24 (.02) | 0.22 (.01) | 0.27 (.03) |
| Urine spiked to 0.405 mg/dL Hb | 0.22 (.02) | 0.21 (.02) | 0.20 (.02) |
| Urine spiked to 300 mg/dL albumin | 0.43 (.02) | 0.40 (.02) | 0.39 (.02) |
| Urine spiked to 300 mg/dL albumin & 50 mg/dL ascorbate | 0.45 (.01) | 0.41 (.02) | 0.42 (.03) |

Figure 2:
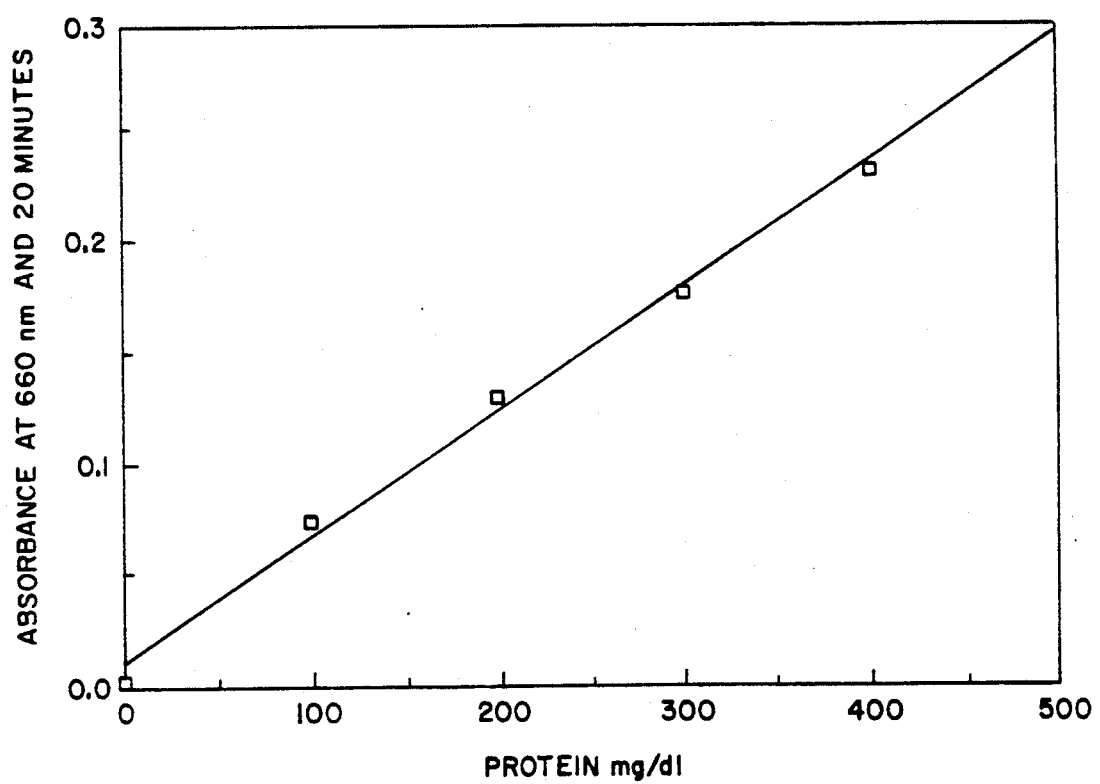
FIG. 2 is a dose response curve of absorbance as a function of protein concentration.

The reaction reaches an endpoint within 5 minutes and, as evidenced by FIG. 1, can be used to quantitate protein concentration. The endpoint absorbance is proportional to protein concentration as shown by the dose-response curve (FIG. 2).

What is claimed is:

1. A method for the detection of a protein in a fluid system which method comprises contacting said fluid with a reagent composition comprising copper in a form capable of forming a copper/protein complex, a peroxide and a redox indicator which produces a detectable response when oxidized by the peroxide in the presence of the copper/protein complex together with an ionizable phosphate containing compound which compound is:

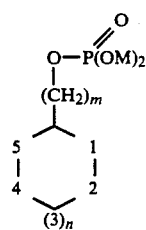

A.

wherein 2, 3, 4 and 5 are selected from the group consisting of

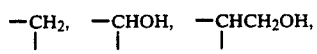

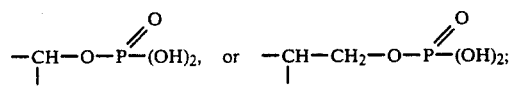

1 is any of the above or —O— and m and n are independently 0 or 1; or

B.

wherein R is OH or substituted or unsubstituted phenyl and M is H or a metallic cation.

2. The method of claim 1 wherein the ionizable phosphate containing compound is phytic acid, 6-glucose phosphate or 1-glucose phosphate.

3. The method of claim 2 wherein the phosphate containing compound is phytic acid.

4. The method of claim 1 wherein the phosphate containing compound is D-ribose-5-phosphate, 6-ribose-1-phosphate, 2,4-cyclopentane diphosphate or 1,4-anhydro-L-threitol diphosphate.

5. The method of claim 1 wherein the ionizable phosphate is

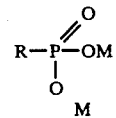

wherein R is substituted or unsubstituted phenyl.

6. The method of claim 1 wherein the copper is derived from coprous sulfate, coprous acetate, coprous citrate, coprous oxalate, coprous phosphate or coprous tartrate.

7. The method of claim 1 wherein the peroxide is cumene hydroperoxide, t-butyl hydroperoxide, diisopropylbenzene hydroperoxide, 1-hydroxycyclohexane-1-hydroperoxide, 2,5-dimethylhexane-2,5-dihydroperoxide, paramenthane hydroperoxide, 1,4-diisopropylbenzene monohydroperoxide, p-t-butylisopropylbenzene hydroperoxide, 2-(α-hydroperoxyisopropyl)-6-isopropylnaphthalene, tetralin hydroperoxide or combinations thereof.

8. The method of claim 1 wherein the redox indicator is benzidine; o-tolidine; a 3,3',5,5'-tetraalkylbenzidine, wherein the alkyl group includes from one to about six carbon atoms; o-dianisidine; 2,7-diaminofluorene; bis-(N-ethyl-quinol-2-one)-azine; (N-methylbenzthiazol-2-one)-(1-ethyl-3-phenyl-5-methyltriazol-2-one)-azine; or combinations thereof.

9. The method of claim 1 wherein the reagent composition is incorporated into a carrier matrix in the form of a reagent strip.

10. A method for the detection of a protein in a fluid system which method comprises contacting said fluid with a reagent composition comprising copper sulfate, diisopropylbenzene dihydroperoxide, 3,3',5,5'-tetramethylbenzidine and phytic acid at a pH greater than 5.0.

11. A reagent system which comprises copper in a form capable of forming a copper/protein complex when contacted with protein in solution, a peroxide, a redox indicator which produces a detectable response when oxidized by the peroxide in the presence of the peroxidatively active copper/protein complex and an ionizable phosphate containing compound which compound is:

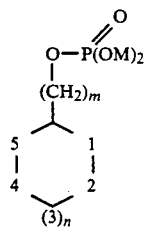   A.

wherein 2, 3, 4 and 5 are selected from the group consisting of

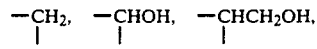

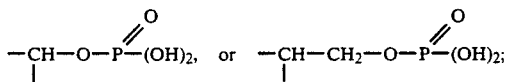

1 is any of the above or —O— and m and n are independently 0 or 1; or

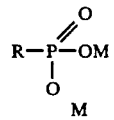   B.

wherein R is OH or substituted or unsubstituted phenyl and M is H or a metallic cation.

12. The method of claim 1 wherein the fluid is urine and the protein is albumin.

* * * * *